United States Patent
Fautz et al.

(10) Patent No.: US 12,228,627 B2
(45) Date of Patent: Feb. 18, 2025

(54) METHOD FOR DETERMINING AN OPTIMIZED SUBSET OF COIL ELEMENTS FROM A PLURALITY OF COIL ELEMENTS FOR CAPTURING A MAGNETIC RESONANCE TOMOGRAPHY RECORDING

(71) Applicant: Siemens Healthcare GmbH, Erlangen (DE)

(72) Inventors: Hans-Peter Fautz, Forchheim (DE); Stephan Kannengiesser, Wuppertal (DE); Jeanette Lenger, Wuerzburg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 242 days.

(21) Appl. No.: 17/942,279

(22) Filed: Sep. 12, 2022

(65) Prior Publication Data
US 2023/0078611 A1 Mar. 16, 2023

(30) Foreign Application Priority Data
Sep. 14, 2021 (DE) .................... 10 2021 210 162.3

(51) Int. Cl.
  *G01R 33/54* (2006.01)
  *A61B 5/055* (2006.01)
(52) U.S. Cl.
  CPC .............. *G01R 33/54* (2013.01); *A61B 5/055* (2013.01); *A61B 2576/00* (2013.01)
(58) Field of Classification Search
  None
  See application file for complete search history.

(56) References Cited

U.S. PATENT DOCUMENTS

| | | | |
|---|---|---|---|
| 10,393,841 B2 * | 8/2019 | Huang | ................. G01R 33/543 |
| 2010/0264923 A1 * | 10/2010 | Heberlein | .......... G01R 33/5611 |
| | | | 324/309 |
| 2011/0006766 A1 | 1/2011 | Jurrissen et al. | |
| 2019/0369180 A1 | 12/2019 | Chang et al. | |

(Continued)

OTHER PUBLICATIONS

Pruessmann K. et al.:"SENSE: Sensitivity Encoding for Fast MRI", Magnetic Resonance in Medicine 42:952-962 (1999).

(Continued)

*Primary Examiner* — Rodney E Fuller
(74) *Attorney, Agent, or Firm* — Harness, Dickey & Pierce, P.L.C.

(57) ABSTRACT

A computer-implemented method for determining a subset of coil elements for capturing a magnetic resonance tomography recording, comprises: providing a target volume in a scout view, and determining a plurality of subsets of coil elements from among the plurality of coil elements, wherein individual subsets are configured different from one another. The method further comprises: determining at least one quality criterion for each subset of coil elements, wherein the at least one quality criterion of a corresponding subset of coil elements relates to an image quality in the target volume, dependent upon the corresponding subset of coil elements; determining the subset of coil elements from the plurality of subsets, based on the corresponding at least one quality criterion; and providing an information item regarding which of the plurality of coil elements are included by the subset of coil elements.

13 Claims, 4 Drawing Sheets

(56) References Cited

U.S. PATENT DOCUMENTS

2019/0369181 A1* 12/2019 Chang .............. G01R 33/56572
2019/0369198 A1* 12/2019 Chang ................ G01R 33/3664

OTHER PUBLICATIONS

Robson, Phillip M et al: "Comprehensive quantification of signal-to-noise ratio and g-factor for image-based and k-space-based parallel imaging reconstructions"; Magnetic Resonance in Medicine; An Official Journal of the International Society for Magnetic Resonance in Medicine; 2008, 60. Jg .; Nr. 4, pp. 895-907.

Blalock, Davis: "Multiplying Matrices Without Multiplying"; In: International Conference on Machine Learning. PMLR; 2021; pp. 992-1004.

Breuer, Felix A.et al. "General Formulation for Quantitative G-factor Calculation in GRAPPA Reconstructions", in: Magentic Resonance in Medicine, vol. 62, pp. 739-746, 2009 // DOI:10.1002/mrm. 22066.

* cited by examiner

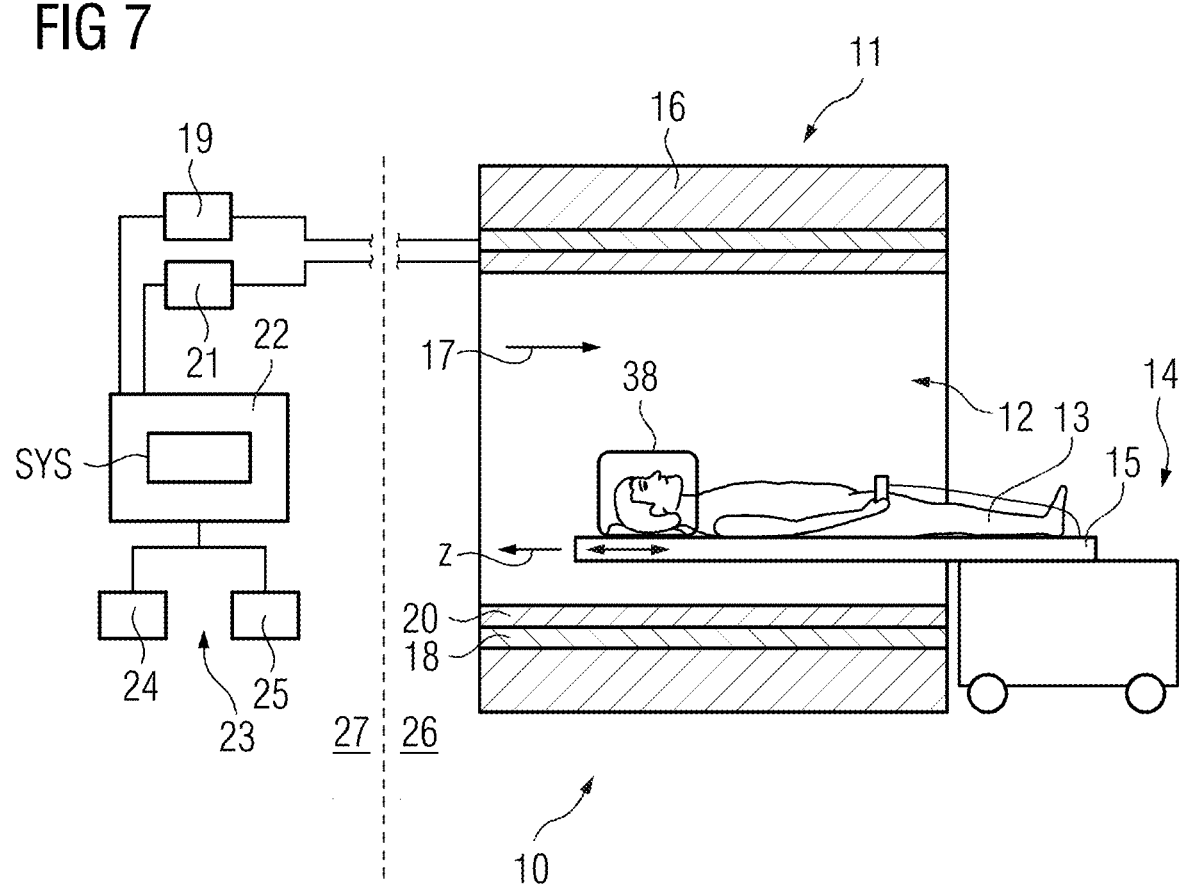

METHOD FOR DETERMINING AN OPTIMIZED SUBSET OF COIL ELEMENTS FROM A PLURALITY OF COIL ELEMENTS FOR CAPTURING A MAGNETIC RESONANCE TOMOGRAPHY RECORDING

CROSS-REFERENCE TO RELATED APPLICATION(S)

The present application claims priority under 35 U.S.C. § 119 to German Patent Application No. DE 10 2021 210 162.3, filed Sep. 14, 2021, the entire contents of which are incorporated herein by reference.

FIELD

One or more example embodiments of the present invention relate to a method for determining an optimized subset of coil elements from a plurality of coil elements for capturing a magnetic resonance tomography recording. One or more example embodiments of the present invention also relate to a determining system which is designed to carry out the method. One or more example embodiments of the present invention also relate to a magnetic resonance tomography system which comprises a determining system according to one or more example embodiments of the present invention. One or more example embodiments of the present invention further relate to a method for providing a trained function, to a computer program product and to a computer-readable storage medium.

BACKGROUND

In the capture of a magnetic resonance tomography (MRT) recording, typically, spins or nuclear spins of a plurality of protons of an examination object, in particular a patient, are aligned in a magnetic field and/or a main magnetic field. The main magnet field typically has a field strength of between 0.2 tesla and 7 tesla and is generated by a main magnet. A frequency of the spin, the Larmor frequency is dependent on the strength of the applied main magnet field. By way of a high frequency pulse or excitation pulse, the spins are synchronized and tilted relative to the applied main magnet field. The spins of identical phase emit a radio signal or signal or electromagnetic signal which can be received or captured with an antenna. After the end of the excitation pulse, the spins slowly align themselves again along the main magnet field and thereby dephase. This process is also referred to as "relaxation". The speed at which the spins align themselves again along the main magnet field and with which the spins dephase therein depends on a material and/or tissue of the examination object that surrounds the spins. The captured signal can, in particular, map the speed of the dephasing and/or the speed at which the spins align in the main magnet field. By applying a magnetic field gradient, the signal can additionally be spatially encoded.

The antenna is typically at least one coil element which is designed to capture or receive the signal. In order to obtain the best possible signal quality, the at least one coil element is positioned as close as possible to the examination object. The further the coil element is from a location in the examination object from which the signal is emitted, the greater is a noise level in the signal captured by the coil element.

In order to capture an MRT recording, typically at least one local coil is positioned on the examination object. The local coil comprises a plurality of coil elements. In order to achieve the best possible signal-to-noise ratio (SNR), the signal is typically captured with a subset or selection of the coil elements of the at least one local coil. Therein, the subset comprises at least one selected coil element.

The suitable selection of the at least one selected coil element is therefore of particular significance for the SNR.

In particular, in a parallel MRT imaging process, the suitable selection of the at least one selected coil element is of great significance in order to ensure an image quality despite the parallelizing during the capturing of the signal. A selection of too few coil elements would slow down the parallel imaging or would make a reconstruction of the MRT recording impossible. A selection of too many coil elements which are possibly already too far removed from the site that is emitting the signal would increase the noise level on the signal and would possibly make a reconstruction of the MRT recording difficult.

It is known to determine the subset of the coil elements and/or the at least one selected coil element manually. In particular, the subset is manually selected and/or determined by a user and/or medical operating personnel member, for example, a Medical-Technical Radiology Assistant (MTRA) or a medical practitioner, in particular a radiologist. Therein the at least one selected coil element of the subset is typically selected and/or determined dependent upon a distance of the at least one selected coil element from the site at which the signal is emitted.

SUMMARY

The process of manual selection and/or determination of the subset can be time-consuming. In addition, manual selection is error-prone. An unsuitable subset can result in a poor SNR. Alternatively or additionally, an unsuitable subset can result in imaging artifacts in a parallel MRT imaging process.

It is therefore an object of one or more example embodiments of the present invention to provide a method which enables an automated determination of the optimized subset, taking account of an image quality of the MRT recording.

According to one or more example embodiments of the present invention, the object is achieved by way of a method for determining an optimized subset of coil elements from a plurality of coil elements for capturing a magnetic resonance tomography recording, by way of a method for determining a trained function, by way of a determining system for determining an optimized subset of coil elements from a plurality of coil elements for capturing a magnetic resonance tomography recording, by way of a magnetic resonance tomography system, by way of a computer program product and by way of a computer-readable storage medium. Advantageous developments are disclosed in the following description.

An inventive achievement of the object, according to one or more example embodiments of the present invention, is described below, both in relation to the claimed devices and also in relation to the claimed method. Features, advantages or alternative embodiments mentioned herein are also transferable similarly to the other claimed subject matter and vice versa. In other words, the object-related claims (which are directed, for example, to a device) can also be further developed with the features disclosed or claimed in relation to a method. The corresponding functional features of the method are thereby embodied by corresponding physical modules.

Furthermore, the inventive achievement of the object, according to one or more example embodiments of the present invention, is described both in relation to methods and devices for providing an optimized subset of coil elements from a plurality of coil elements for capturing a magnetic resonance tomography recording as well as in relation to methods and devices for providing a trained function. Herein, features and alternative embodiments of data structures and/or functions in methods and devices for the determining can be transferred to analogous data structures and/or functions in methods and devices for adjusting/optimizing/training. Analogous data structures can herein be characterized, in particular, by the use of the qualifier "training". Furthermore, the trained functions used in methods and devices for determining an optimized subset of coil elements from a plurality of coil elements for capturing a magnetic resonance tomography recording can have been trained and/or adjusted and/or provided, in particular, by way of methods for providing the trained function.

One or more example embodiments of the present invention relates to a computer-implemented method for determining an optimized subset of coil elements from a plurality of coil elements for capturing a magnetic resonance tomography recording. The method comprises a method step of providing a target volume in a scout view. The method further comprises a method step of determining a plurality of subsets of coil elements of the plurality of coil elements. Therein, the individual subsets of the plurality of subsets are configured different from one another. The method further comprises a method step of determining at least one quality criterion for each subset of coil elements. Therein, the at least one quality criterion of a subset of coil elements relates to an image quality in the target volume, dependent upon the corresponding subset of coil elements. The method further comprises a method step of determining the optimized subset of coil elements from the plurality of subsets, dependent upon the corresponding quality criteria. The method further comprises a method step of providing an information item regarding which of the plurality of coil elements are included by the optimized subset of coil elements.

On capturing the magnetic resonance tomography (MRT) recording, as described above, a radio signal or signal is captured and/or received. The signal is emitted by a plurality of spins or nuclear spins of protons which, after excitation by way of a high-frequency excitation pulse in a magnetic field and/or main magnet field, relax. Therein, the protons are arranged in an examination object which is positioned in the main magnet field. The examination object is therein positioned, in particular, in a tubular opening of an MRT system. The examination object can be a human, in particular a patient, or an animal.

The plurality of coil elements are therein configured to capture or receive the signal during capturing of the magnetic resonance tomography (MRT) recording. The plurality of coil elements can therein be included by at least one local coil. The coil elements and/or the at least one local coil can therein be arranged on the examination object. The coil elements can therein be actuated and/or read out individually.

In the method step of providing the target volume in the scout view, the target volume is received or captured or called up or determined.

Therein, the scout view maps the examination object or at least a portion of the examination object that is arranged in the main magnet field. The scout view maps the examination object and/or the portion of the examination object in a three-dimensional voxel matrix and serves for further planning of the examination. The scout view does not have to meet any particular requirements with regard to resolution or signal-to-noise ratio. The scout view can be, in particular, a rapid MRT recording with low spatial resolution.

The scout view can be captured or have been captured, in particular, with a system antenna or system coil or high frequency antenna unit. The system coil is therein arranged, in particular, in a housing of the MRT system. The system coil can, in particular, also be configured to emit the high frequency excitation pulse for exciting the spin. The system coil is therein arranged, in particular, at a relatively large distance from the examination object. A quality and/or image quality of the scout view can be reduced, in particular, on the basis of the distance. Due to the large distance, the image quality of the scout view is homogeneous over a field of view. The field of view defines the region and/or portion of the examination object that is mapped in the scout view.

The target volume defines a region of the examination object in the scout view. In particular, the target volume defines a three-dimensional volume of the examination object which is mapped in the scout view. The target volume can therein comprise, in particular, a portion of or the whole voxel matrix of the scout view. The region of the examination object in the target volume can be relevant, in particular, for a diagnosis and/or an investigation and/or a medical intervention. Therein, the diagnosis and/or investigation and/or the medical intervention can be based upon the MRT recording that is to be captured. In particular, the best possible image quality is necessary, particularly in the region of the target volume.

The target volume can be captured, in particular, in the step of providing. For example, therein the target volume can be specified and/or selected in the scout view by a user, for example, an MTRA or a medical practitioner. In particular, the target volume can then be received via a user input. The user input can take place, for example, via a touch-sensitive screen (touchscreen).

Alternatively, the target volume can be segmented in an automated manner. In particular, the segmented target volume can be received in the method step of providing the target volume in relation to the scout view.

In the method step of determining the plurality of subsets of coil elements, the plurality of subsets are determined from the plurality of coil elements.

Therein, two subsets differ from one another in each case. In other words, each subset comprises a different combination and/or selection of coil elements from the plurality of coil elements. In other words, each subset is unique within the plurality of subsets. Each subset therein comprises at least one coil element. In particular, during parallel imaging, each subset can comprise at least two coil elements. A single coil element can therein be included in more than one subset.

In particular, the plurality of subsets can comprise all the possible combinations of coil elements of the plurality of coil elements. Alternatively, the plurality of subsets can comprise a selection of possible combinations of coil elements of the plurality of coil elements.

In the method step of determining at least one quality criterion, for each subset, that is, for each combination of coil elements included by a subset, at least one quality criterion is determined.

The at least one quality criterion of a subset therein relates to and/or defines an expected image quality of an MRT recording that is captured with the corresponding subset of coil elements in the target volume. In other words, the quality criterion of a subset defines what image quality an MRT recording would have in the target volume if it were captured with the at least one coil element of the subset.

The image quality is therefore an expected image quality. The image quality can depend, in particular, on the subset and/or the combination and/or the selection of coil elements.

In particular, the quality criterion can be determined dependent upon known quality features of the individual coil elements. In other words, the quality criterion of a subset can be derived from the quality feature of the at least one coil element of the subset.

In particular, the quality criterion can be determined on the basis of a knowledge of the position of the coil elements in the scout view and the target volume. In other words, the quality criterion can take account of a position of the examination object, in particular the target volume, relative to the coil elements of the subset.

In some embodiments of the present invention, the quality criterion can take account of an expected duration and/or recording duration of the capturing of the MRT recording with the corresponding subset of coil elements. In particular, a recording duration which exceeds a threshold value can have a negative influence on the quality criterion.

In the method step of determining the optimized subset of coil elements, the optimized subset is determined dependent upon the quality criteria of the subsets from the plurality of subsets.

In particular, the subset, the quality criterion of which is optimal and/or is best as compared with the other quality criteria of the other subsets, can be determined as an optimized subset. In particular, the quality criterion is then best in relation to the target volume and/or is optimized. In particular, with the optimized subset of coil elements, the best expected image quality of the MRT recording can be achieved. In particular therein, in some embodiments of the present invention, the recording duration for capturing the MRT recording can be taken into account.

In the method step of providing the information as to which of the plurality of coil elements are included by the optimized subset, the information is provided as to which coil elements and/or which at least one coil element is to be used and/or read out according to the optimized subset for capturing the MRT recording. In particular, the information is provided as to which coil elements are to be read out on capturing of the MRT recording in order to ensure an optimized image quality. In other words, the information is provided as to which at least one coil element and/or which coil elements of the plurality of coil elements are included by the optimized subset.

The inventors have discovered that, dependent upon known properties of the coil elements, a quality criterion can be determined for each of the subsets of coil elements. By way of taking account of the quality criterion during determination of the optimized subset, a suitable selection of coil elements can be ensured for capturing the MRT recording. The inventors have discovered that the determination of the optimized subset can be accelerated and is less fault-prone as compared with the manual selection. The inventors have discovered that when determining the optimized subset of coil elements, it is ensured, dependent upon the quality criterion and/or the quality criteria, that the image quality at least in the target volume is suitable for further medical analyses. The inventors have discovered that it is sufficient if the quality criterion in relation to the target volume is taken into account. In particular, in this way it can be prevented that a subset is selected, which is optimized for a region different from the target volume. In particular, the dependency of the image quality of a subset on the position of the coil elements of the subset is taken into account. The inventors have also discovered that the duration of the capturing of the MRT recording during determination of the quality criterion can be taken into account. In this way, a comfort of the examination object can be ensured during capturing of the MRT recording.

According to one aspect of an embodiment of the present invention, the method also comprises a method step of capturing the magnetic resonance tomography recording with the optimized subset of coil elements.

In particular, during capturing of the MRT recording, the coil elements that are included by the optimized subset are read out. In particular, in the step of providing the information as to which coil elements are included by the optimized subset, the information is provided to an MRT system for capturing the MRT recording. In particular, the MRT system is controlled such that the signal is read out during capturing of the MRT recording by the coil elements of the optimized subset.

In particular, in the method step of capturing the MRT recording, the MRT recording is reconstructed from the signal captured with the at least one coil element of the optimized subset. In particular, in the step of capturing the MRT recording, the three-dimensional MRT recording is reconstructed from the captured signal and/or the raw data. In particular, the MRT recording can be reconstructed from the captured signal on the basis of the filtered back projection. The MRT recording then maps structures of the examination object in a three-dimensional recording.

In particular, therefore, the method step of capturing the MRT recording can comprise a method step of reading out the coil elements and/or the at least one coil element of the optimized subset and a method step of reconstructing the MRT recording from the captured and/or read-out signal.

The inventors have discovered that an optimized MRT recording can be captured with knowledge of the optimized subset. The inventors have discovered that, in this way, a quality assurance can be provided on capturing MRT recordings.

According to a further aspect of an embodiment of the present invention, the target volume comprises one of the following regions: a field of view of the scout view, a segmented organ mapped in the scout view, a cuboid about an organ mapped in the scout view or a region of the scout view relevant for a diagnostic process.

The field of view of the scout view therein defines the whole of the region and/or portion of the examination object that is mapped in the scout view.

The segmented organ can be, for example, a heart or a liver or a lung or a kidney or a stomach or a gut, etc. of the examination object. Alternatively, the organ can be a portion of a skeleton of the examination object, for example, one or more vertebrae of the spinal column. The organ can, in particular, be segmented automatically in the scout view. For this purpose, a segmentation algorithm can be used on the scout view. The segmentation algorithm can segment the organ on the basis of a threshold value segmentation. Alternatively, the segmentation algorithm can comprise a trained function which is designed and/or trained to segment the organ in the scout view. Alternatively, the organ can be segmented manually by the user, in particular by the MTRA or the medical practitioner.

The cuboid about the mapped organ can be, in particular, a simplified segmentation. In particular, the cuboid comprises the three-dimensional target volume. The organ is situated within the cuboid. In particular, the cuboid can be configured such that it forms the smallest possible volume which includes the whole organ in the scout view. In particular, the cuboid can be automated, for example, with a trained function, or can be determined manually.

The region of relevance for diagnostics can comprise, in particular, any desired structure of the examination object. For example, the region of relevance for diagnostics can comprise an organ. In particular, the region of relevance for diagnostics can comprise unspecified tissue structures, for example, in the region of an organ. The diagnostic process can comprise, in particular, the creation of a diagnosis for the examination object dependent upon the MRT recording. Alternatively, the diagnostic process can also comprise monitoring of a medical intervention, in particular a surgical and/or minimally invasive intervention. In particular, the region to be monitored is then mapped in the MRT recording.

In some embodiments, the target volume configured as described above can be determined by way of applying a trained function to at least the scout view. In particular, in addition to the scout view the trained function can be applied to an information item relating to a purpose of the MRT recording and/or a target of the examination or a key expression relating to the diagnostics. For example, the trained function can be applied to a scout view of a thorax and the key expression "spinal disk". Then the target volume determined by the trained function can comprise the segmented spinal column. A general description of a trained function follows in the next part of the description.

The inventors have discovered that the target volume depends upon the requirements placed upon the MRT recording. The inventors have discovered that with knowledge of the requirements and/or the target volume, the optimized subset is directly adaptable to the requirements. In particular, the optimized subset is determined dependent upon the target volume.

According to a further aspect of an embodiment of the present invention, the method step of determining the optimized subset comprises a method step of applying a trained function to the quality criteria of the plurality of subsets of coil elements. Therein, an optimized quality criterion is determined. Therein, the optimized subset is the subset corresponding to the optimized quality criterion.

In general, a trained function emulates cognitive functions that link human thinking to humans. In particular, by way of training based upon training data, the trained function can adapt to new circumstances and can recognize and extrapolate patterns.

In general, parameters can be adapted to a trained function via training. In particular, for this purpose, a monitored or supervised training, a semi-supervised training, an unsupervised training, a reinforcement learning and/or an active learning process can be used. Furthermore, representation learning (an alternative expression is "feature learning"), can be used. In particular, the parameters of the trained functions can be adapted iteratively by way of a plurality of training steps.

In particular, a trained function can comprise a neural network, a support vector machine, a random tree and/or a decision tree and/or a Bayesian network, and/or the trained function can be based upon k-means clustering, Q-learning, genetic algorithms and/or association rules. In particular, a trained function can comprise a combination of a plurality of uncorrelated decision trees and/or an assembly of decision trees (a random forest). In particular, the trained function can be determined via XGBoosting (Extreme Gradient Boosting). In particular, a neural network can be a deep neural network, a convolutional neural network or a convolutional deep neural network. Furthermore, a neural network can be an adversarial network, a deep adversarial network and/or a generative adversarial network. In particular, a neural network can be a recurrent neural network. In particular, a recurrent neural network can be a network with long-short-term memory (LSTM), in particular, a gated recurrent unit (GRU). In particular, a trained function can comprise a combination of the described approaches. In particular, the approaches described here are specified for a trained function network architecture of the trained function.

In particular, the input data of the trained function are the quality criteria of the plurality of subsets. In other words, the trained function is applied to the entirety of the at least one quality criterion of each subset of the plurality of subsets. Therein, the optimized quality criterion is determined. The optimized quality criterion is therein one of the quality criteria of all the subsets. The optimized quality criterion can predict, for example, in comparison with other quality criteria, the best image quality to be expected for the corresponding subset of coil elements. In some embodiments of the present invention, for example, a duration for capturing the corresponding MRT recording with the corresponding subset of coil elements can be taken into account.

The optimized subset is then the subset of the plurality of subsets for which the optimized quality criterion has been determined. In other words, the optimized quality criterion is assigned to the optimized subset.

The inventors have discovered that by way of using a trained function, the optimized subset can be determined automatically. The inventors have discovered that a large amount of experience exists in the manual selection of the optimized subset, which can be used for training the trainable function. In this way, the method step of determining the optimized subset can be accelerated as compared with the manual selection. The inventors have additionally discovered that by way of using the trained function for determining the optimized subset, a comparability between different MRT recordings on the basis of the automated uniform determination of the optimized subset is better than for a manual selection.

According to a further aspect of an embodiment of the present invention, the at least one quality criterion of a subset of the plurality of subsets relates to noise in a magnetic resonance tomography recording captured with the subset.

In particular, the quality criterion of a subset can comprise a noise and/or a noise level and/or a noise quantity in the signal captured and/or received with the at least one coil element of the subset. In other words, the quality criterion can comprise a noise level in the raw data of the captured signal.

Alternatively or additionally, the quality criterion of a subset can comprise a noise and/or a noise level in a reconstructed MRT recording captured with the at least one coil element. In other words, the quality criterion can comprise a noise level in the reconstructed data and/or medical image data on the basis of the raw data.

In particular, the noise and/or the noise level can specify a mean noise in the target volume. Alternatively, the noise and/or the noise level can specify a variance of the noise in the target volume. Alternatively, the noise and/or the noise level can be spatially resolved at least over the target volume. In other words, an expected noise in each voxel of at least the target volume of the scout view can be specified by way of the noise and/or the noise level.

Alternatively or additionally, the quality criterion of a subset can comprise an information item regarding a possibility and/or a probability of an artifact-free or artifact-reduced reconstruction of the signal captured with the at least one coil element. In this case, the expression "noise" can also define a probability of the occurrence of one or more artifacts in the MRT recording. In particular, the probability can be a mean probability in the target volume or a variance of the probability in the target volume or a spatially resolved probability at least in the target volume.

The inventors have discovered that the (expected) image quality of the MRT recording can be described by way of a noise. The inventors have discovered that the noise is a readily comparable quality criterion. In particular, the inventors have discovered that the noise influences a feature for the reconstructability of the MRT recording from the captured signal and/or the raw data. The inventors have also discovered that the reconstructability is relevant in the form of the noise level and/or in the form of a probability of the occurrence of artifacts, in particular, in parallel MRT imaging.

According to a further aspect of an embodiment of the present invention, in the method step of determining the optimized subset, the subset of the plurality of subsets is determined, according to the quality criterion of which the noise is minimal compared with the quality criteria of the other subsets.

In particular, therein, the noise and/or the noise level can be quantitatively compared in the target volumes for the different subsets.

In particular, the mean noise in the target volume can be minimal for the optimized subset. Alternatively, a variance of the noise in the target volume can be minimal for the optimized subset.

In particular, the noise can be compared on a spatially resolved basis. In particular, the noise can be minimal if the noise over the target volume is minimal.

In particular, as described above, the noise can also be a probability for an artifact-free or artifact-reduced reconstruction. In particular, the quality criterion of the optimized subset and/or the optimized quality criterion can comprise the comparatively minimal probability for an occurrence of an artifact in the reconstruction. Thus a reconstructability of the signal included with the optimized subset of coil elements is maximal.

The inventors have discovered that the noise can be minimized by way of the optimized selection of coil elements and/or by way of the optimized subset. The inventors have discovered that in this way, the image quality of the MRT recording can be optimized. The inventors have discovered that on the basis of the expected noise, the optimized subset can be determined in advance of the capturing of the MRT recording.

According to a further aspect of an embodiment of the present invention, the at least one quality criterion of each subset comprises a g-factor map.

A g-factor map defines a spatially resolved noise amplification over the field of vision of a subset of coil elements dependent upon the combination of coil elements of the subset. The g-factor map can therein be derived from a combination of the spatially resolved sensitivity maps of all the coil elements in the subset.

The g-factor map is significant, in particular, in parallel MRT imaging. The g-factor can also be designated a geometry factor. From the g-factor map, a reconstructability and/or a quality of the reconstructed MRT recording can be derived. The g-factor map can depend, in particular, on an acceleration factor during capturing of the MRT recording via parallel imaging. The g-factor map defines, in particular (at least qualitatively) in a spatially resolved manner what noise is to be expected in the reconstructed MRT recording. A detailed description regarding g-factor maps is given, for example, by Breuer et al. in "General Formulation for Quantitative G-Factor Calculation in GRAPPA Reconstructions", Magnetic Resonance in Medicine 62: 739-746 (2009).

A coil element is particularly sensitive to signals in its close vicinity. The sensitivity decreases with a distance from the coil element. This behavior can be described in a sensitivity map for the coil element.

In order to determine the sensitivity map of a coil element, a further rapid scout view can be recorded with the corresponding coil element. Therein, only the signal of the individual coil element is read out. This scout view can then be divided by the scout view that was captured with the system coil. In this way, the sensitivity of the coil element can be put into relation with the sensitivity of the system coil. In other words, the sensitivity map of a coil element corresponds to the quotient of the scout view captured with the coil element and the scout view captured with the system coil.

In particular, at least for each coil element which is included by a subset, a sensitivity map of this type can be determined.

For each subset, the g-factor map can be determined from the sensitivity maps of the coil elements included by the subset. In particular, for this purpose for example, the values of a g-factor map can be calculated from the values of the sensitivity maps of the individual coil elements with the aid of a mathematical formula. This can take place directly or via reconstruction coefficients of the parallel MRT imaging. Therein, an acceleration factor can be taken into account which specifies a degree of parallelization. With an acceleration factor equal to 1, the MRT imaging is not parallelized and thus corresponds to the standard MRT imaging. The determination of the g-factor map (dependent upon the degree of parallelization) is described, in particular, by Breuer et al. in "General Formulation for Quantitative G-Factor Calculation in GRAPPA Reconstructions", Magnetic Resonance in Medicine 62: 739-746 (2009) or by Pruessmann et al. "SENSE: Sensitivity Encoding for FAST MRT", Magnetic Resonance in Medicine 42: 952-962 (1999).

On determination of the g-factor map, the individual sensitivity maps can be placed in a spatial relation to one another. In particular, the sensitivity maps are registered spatially to one another.

In particular, a sensitivity map can comprise a plurality of voxels which are arranged in a voxel matrix. In particular, each voxel comprises a voxel value. In the registration of two sensitivity maps, to each voxel of the one sensitivity map, a voxel of the other sensitivity map is assigned. Therein, the voxels assigned to one another map the sensitivity of the corresponding coil elements at the same location. The location relates therein to the MRT system. The voxel values of the voxels assigned to one another are correspondingly offset against one another. In particular, the g-factor map then comprises a plurality of voxels which are arranged in a corresponding voxel matrix.

In particular, in this exemplary embodiment, the method step of determining the at least one quality criterion can comprise the following method steps:
    capturing a scout view with the system coil, wherein this scout view can correspond to the scout view described above, capturing further scout views with each individual coil element of the plurality of coil elements, determining a sensitivity map for each coil element, wherein the sensitivity map of a coil element is a quotient of the scout view of the corresponding coil element and the scout view captured with the system coil, determining the g-factor maps for each subset of coil elements on the basis of the sensitivity maps of the coil elements included by the individual subsets.

The inventors have discovered that the g-factor maps can be determined easily and rapidly for the different subsets of coil elements from the sensitivity maps. The inventors have discovered that the g-factor maps describe the expected image quality well. The inventors have discovered that the g-factor maps are of great significance, in particular, for the image quality.

According to a further aspect of an embodiment of the present invention, the at least one quality criterion of each subset relates to a combined sensitivity map for the coil elements of the subset.

The combined sensitivity map of a subset defines a sensitivity of the coil elements of the subset. In other words, the combined sensitivity map defines how the sensitivities of the individual coil elements of the subset are brought together and/or combined to form an overall sensitivity. The combined sensitivity map defines, in particular, a spatial distribution of the combined overall sensitivity.

In particular, the combined sensitivity map can comprise, as described above in relation to the sensitivity maps of the individual coil elements, a plurality of voxels which are arranged in a voxel matrix. Therein, each voxel comprises a voxel value.

For each subset of coil elements, a combined sensitivity map is determined. The determination of the combined sensitivity map of a subset can therein comprise the following method steps:

capturing a scout view with the system coil, wherein this scout view can correspond to the scout view described above, capturing a further scout view with the combination of coil elements of the plurality of coil elements which are included by the subset, determining the combined sensitivity map of the subset, wherein the scout view of the subset is divided by the scout view of the system coil.

In particular, therefore, a plurality of combined sensitivity maps can be determined for the plurality of subsets of coil elements.

In particular, the scout views can be captured in parallel with the different subsets. For this purpose, during capturing of the scout view, all the coil elements can be read out separately. In order to determine the scout view of a particular subset, the read-out signals of the coil elements included by the subset are combined and the scout view is reconstructed from the combined signal. The combining takes place via mathematical models known from MRT imaging.

In some embodiments of the present invention, the combined sensitivity map of a subset can be put into relation with a noise quantity and/or a noise level of the subset of coil elements. The noise level of a subset can therein define a background noise by way of the examination object and/or by way of the surroundings and/or a system noise.

The noise level of the subset of coil elements can be determined in the following method steps:

capturing a noise signal with each coil element of the subset, wherein on capturing the noise signal, only the main magnet field acts upon the examination object, combining the noise signals of the coil elements of the subset, determining the noise level on the basis of the combined noise signal, wherein the noise level relates, in particular, to a variance and/or a mean value of the combined noise signal.

On combining the noise signals of the individual coil elements, the noise signals can be, in particular, added or averaged or offset against one another in a complex manner. The combining can take place similarly to the combining of the read-out signals on capturing the scout view.

The noise level of the plurality of subsets can be captured in parallel. For this purpose, in the method step of capturing a noise signal, the noise signal can be read out from each individual coil element of the plurality of coil elements which are included by at least one subset. In the method step of determining the combined noise signal, the noise signal for each subset is determined by way of combining the noise signals of the coil elements included by the subset. In particular, in this way for each subset, a noise quantity and/or a noise level can be determined.

In particular, in the combined sensitivity map of each subset, a mean signal can be determined in the target volume or in at least a portion of the target volume. For this purpose, the voxel values are averaged in the target volume or in the at least one portion of the target volume.

For each subset, on the basis of the quotient of the signal and the noise level, a signal-to-noise ratio can then be determined. In particular, the quality criterion of each subset can then comprise the signal-to-noise ratio of the subset.

The inventors have discovered that the combined sensitivity maps enable a prediction regarding the expected image quality of the MRT recording for the different subsets. The inventors have further discovered that the signal-to-noise ratio represents a simple relation in order to quantify the image quality. In particular, on the basis of the signal-to-noise ratio, the quality criteria of the different subsets can easily be compared.

One or more example embodiments of the present invention further relate to a computer-implemented method for providing a trained function for determining an optimized subset of coil elements. The method comprises a method step of providing a plurality of training quality criteria. Each training quality criterion of a planned magnetic resonance tomography recording is therein assigned from a plurality of planned magnetic resonance tomography recordings. The method further comprises a method step of providing a plurality of optimized training quality criteria. Therein, for each planned magnetic resonance tomography recording, an optimized training quality criterion is provided. Therein, the optimized training quality criteria are included by the training quality criteria. The method also comprises a step of training a function dependent upon the plurality of training quality criteria and the plurality of optimized training quality criteria. The method further comprises a method step of providing the trained function.

The training quality criteria can be configured as described above in relation to the quality criteria. Each training quality criterion is therein associated with a training subset of coil elements.

In particular, more than one training quality criterion can be assigned to each planned MRT recording. In other words, the plurality of planned MRT recordings can comprise fewer planned MRT recordings than training quality criteria from the plurality of training quality criteria.

One of the training quality criteria of each planned MRT recording corresponds to one optimized training quality criterion. A corresponding training subset of coil elements is assigned to each optimized training quality criterion. A training subset which is assigned to an optimized training quality criterion is designated an optimized training subset. By way of a determination of the optimized training quality criteria, correspondingly optimized training subsets of coil elements are therefore determined accordingly. In particular, for each planned MRT recording, an optimized training quality criterion and thus an optimized training subset is determined.

In particular, the optimized training quality criterion of a planned MRT recording can be determined and/or selected manually from the training quality criteria assigned to the MRT recording. In particular, the optimized training quality criterion can be determined manually by an experienced user, in particular an MTRA or a medical practitioner. Therein, the determination can be based upon the experience of the user. Alternatively or additionally, for manual determination for each training subset, an MRT recording can be captured. The optimized training subsets can be determined on the basis of the captured MRT recordings. The optimized training quality criteria therein correspond to the training subsets assigned to the optimized training subsets.

In the method steps of providing the plurality of training quality criteria and of providing the plurality of optimized training quality criteria, the plurality of training quality criteria and/or the plurality of optimized training quality criteria can, in particular, be accessed by a server. The server can be, in particular, a cloud server or a local server. In particular, the training quality criteria and/or the optimized training quality criteria on the server can be stored in a database.

The inventors have discovered that the trained function can be trained via monitored learning. The inventors have discovered that for this purpose, the optimized training quality criteria and/or the optimized training subsets can be determined manually for a plurality of planned MRT recordings.

One or more example embodiments of the present invention further relate to a determining system for determining an optimized subset of coil elements from a plurality of coil elements for capturing a magnetic resonance tomography recording. The determining system comprises an interface and a computing unit. Therein, the interface is designed for providing a target volume in a scout view. Therein, the computing unit is designed for determining a plurality of subsets of coil elements of the plurality of coil elements. Therein, the individual subsets of the plurality of subsets are configured different from one another. Therein, the computing unit is also designed for determining at least one quality criterion for each subset of coil elements. Therein, the at least one quality criterion of a subset of coil elements relates to an image quality in the target volume, dependent upon the corresponding subset of coil elements. Therein, the computing unit is furthermore designed for determining the optimized subset of coil elements from the plurality of coil elements dependent upon the corresponding quality criteria. Therein, the interface is furthermore designed for providing an information item as to which of the plurality of coil elements are included by the optimized subset of coil elements.

A determining system of this type can be configured, in particular to carry out the method described above for determining an optimized subset of coil elements from a plurality of coil elements for capturing a magnetic resonance tomography recording and its aspects. The determining system is configured to carry out this method and its aspects in that the interface and the computing unit are configured to carry out the corresponding method steps.

In particular, the description relating to the method can be transferred to the aspects of the determining system.

One or more example embodiments of the present invention further relate to a magnetic resonance tomography system. The MRT system comprises a determining system as described above. Therein, the MRT system is designed for capturing an MRT recording with a subset of the plurality of subsets of coil elements.

The MRT system preferably comprises a medical and/or diagnostic MRT system which is configured and/or designed for capturing medical and/or diagnostic MRT recordings and/or image data of an examination object described above. For this purpose, the MRT system comprises a scanner unit. The scanner unit of the MRT system preferably comprises a detector unit, in particular a magnet unit for capturing the MRT recording. Preferably, the scanner unit herein comprises, in particular, the magnet unit, a main magnet, a gradient coil unit and a system coil and/or a high frequency antenna unit. The system coil is firmly arranged within the scanner unit and is configured and/or designed for emitting an excitation pulse. In order to capture the magnetic resonance signal and/or the radio signal and/or the signal, the MRT system has at least one local coil which can be arranged about a region to be investigated in the examination object.

The main magnet of the scanner unit is configured for generating a homogeneous main magnet field and/or magnetic field with a defined magnetic field strength, for example, with a defined and/or determined magnetic field strength of 3 T or 1.5 T, etc. In particular, the main magnet is configured for generating a strong, constant and homogeneous main magnet field. The homogenous main magnet field is preferably arranged and/or located within a recording region for the examination object of the MRT system. The gradient coil unit is designed for generating magnetic field gradients that are used for position encoding during an imaging process.

The receiving region is designed and/or configured for receiving the examination object, in particular the region of the examination object to be investigated, for a medical MRT examination. For example, for this purpose, the receiving region is configured cylindrical and/or is cylindrically surrounded by the scanner unit. For this purpose, the scanner unit has an enclosure of the housing unit at least partially surrounding the receiving region. The enclosure surrounding the receiving region can herein also be designed in one part and/or integrally with the side of the system coil facing toward the receiving region or can also be designed separately from the system coil of the scanner unit.

A field of view (FOV) and/or an isocenter of the MRT system is preferably arranged within the receiving region. The FOV preferably comprises a capture region of the MRT system, within which the conditions exist for a capture of an MRT recording, in particular MRT image data, such as for example a homogeneous main magnet field. The isocenter of the MRT system preferably comprises the region and/or point within the MRT system which has the optimal and/or ideal conditions for the capture of an MRT recording, in particular, MRT image data. In particular, the isocenter comprises the most homogeneous magnetic field region within the MRT system.

During an MRT examination, the examination object is situated lying on a support within the receiving region of the MRT system. However, a medical operating personnel member and/or the user is situated in a control room which is separate from an examination room in which the MRT system is arranged.

One or more example embodiments of the present invention also relate to a computer program product having a computer program, and also a computer-readable medium. A realization largely through software has the advantage that conventionally used determining systems can also easily be upgraded by way of a software update in order to operate in the manner described. Such a computer program product can comprise, apart from the computer program, possibly additional constituents, such as, for example, documentation and/or additional components as well as hardware components, for example, hardware keys (dongles, etc.) for using the software.

One or more example embodiments of the present invention relate also, in particular, to a computer program product with a computer program which is directly loadable into a memory store of a determining system, having program portions in order to carry out all the steps of the method described above for determining an optimized subset of coil elements from a plurality of coil elements for capturing a magnetic resonance tomography recording and its aspects when the program portions are executed by the determining system.

One or more example embodiments of the present invention further relate, in particular, to a computer-readable storage medium on which program portions that can be read and executed by a determining system are stored, in order to carry out all the steps of the method described above for determining an optimized subset of coil elements from a plurality of coil elements for capturing a magnetic resonance tomography recording and its aspects when the program portions are executed by the determining system.

One or more example embodiments of the present invention further relate to a training system comprising a training interface and a training computing unit. The training interface is designed for providing a plurality of training quality criteria. Each training quality criterion of a planned magnetic resonance tomography recording is therein assigned from a plurality of planned magnetic resonance tomography recordings. The training interface is further designed for providing a plurality of optimized training quality criteria. Therein, for each planned magnetic resonance tomography recording, an optimized training quality criterion is provided. Therein, the optimized training quality criteria are included by the training quality criteria. The training computing unit is designed for training a function dependent upon the plurality of training quality criteria and the plurality of optimized training quality criteria. The training interface is also designed for providing the trained function.

One or more example embodiments of the present invention also relate to a training computer program product having a training computer program, and also a computer-readable training medium. A realization largely through software has the advantage that conventionally used training systems can also easily be upgraded by way of a software update in order to operate in the manner described. Such a training computer program product can comprise, apart from the training computer program, possibly additional constituents, such as, for example, documentation and/or additional components as well as hardware components, for example, hardware keys (dongles, etc.) for using the software.

One or more example embodiments of the present invention also relate, in particular, to a training computer program product with a training computer program which can be directly loaded into a memory store of a training system, having program portions in order to carry out all the steps of the method described above for providing a trained function for determining an optimized subset of coil elements and its aspects when the program portions are executed by the training system.

One or more example embodiments of the present invention also relate, in particular, to a computer-readable training storage medium on which program portions that can be read and executed by a training system are stored, in order to carry out all the steps of the method described above for providing a trained function for determining an optimized subset of coil elements, and its aspects when the program portions are executed by the training system.

BRIEF DESCRIPTION OF THE DRAWINGS

The above described properties, features and advantages of this invention are more clearly and distinctly described in the context of the following description making reference to the drawings. The drawings and descriptions are not intended to restrict the present invention and its embodiments in any way.

In the different figures, the same components are provided with corresponding reference characters. The figures are in general not to scale.

In the figures:

Figure 1:
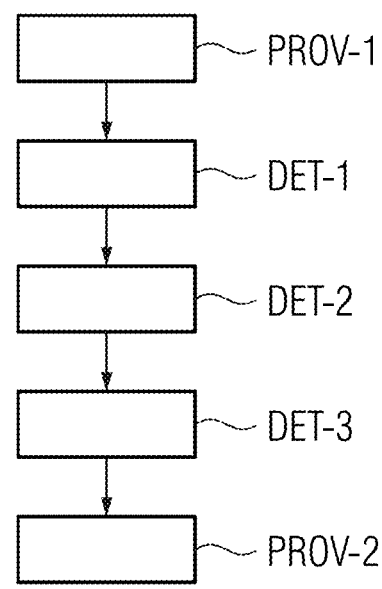
Figure 2:
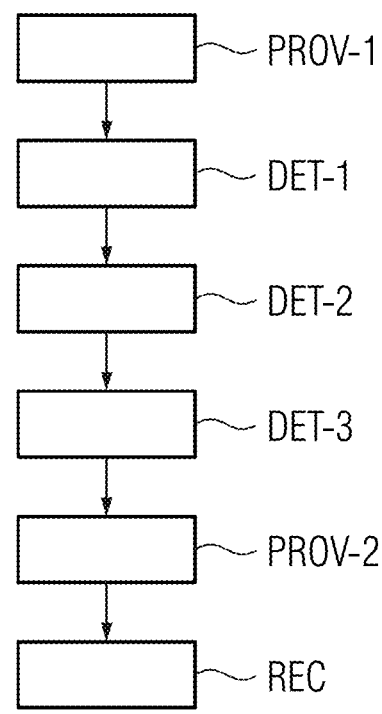
Figure 3:
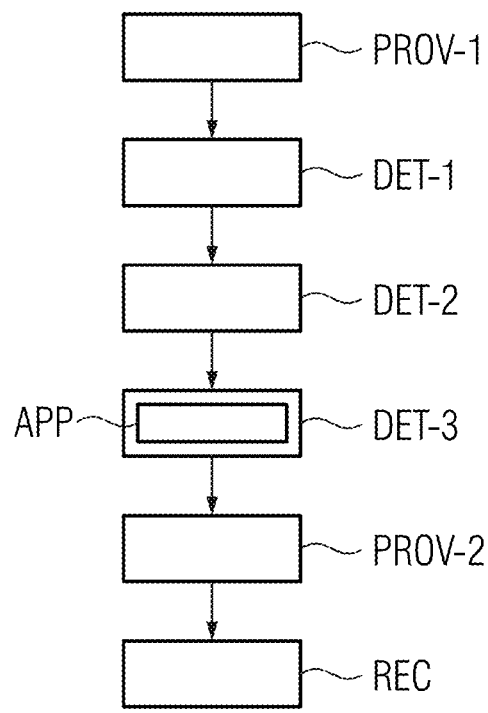
Figure 4:
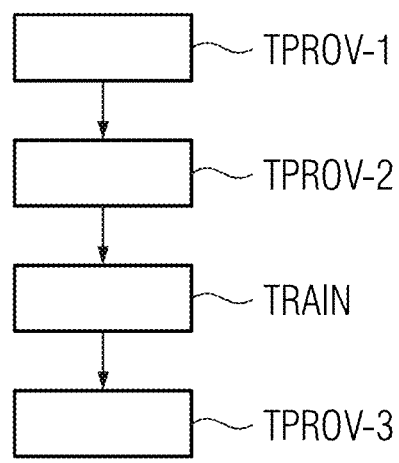
Figure 5:
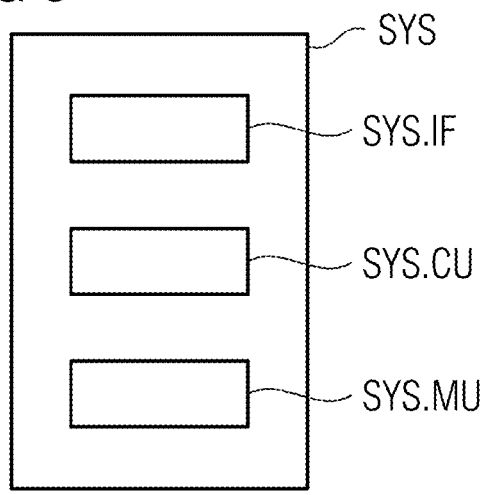
Figure 6:
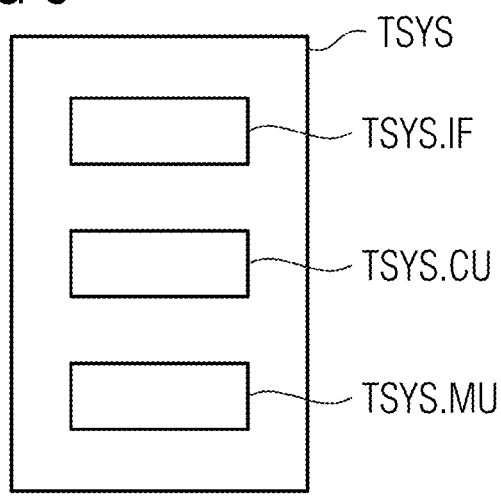

FIG. 1 shows a first exemplary embodiment of a method for determining an optimized subset of coil elements from a plurality of coil elements for capturing a magnetic resonance tomography recording, FIG. 2 shows a second exemplary embodiment of a method for determining an optimized subset of coil elements from a plurality of coil elements for capturing a magnetic resonance tomography recording, FIG. 3 shows a third exemplary embodiment of a method for determining an optimized subset of coil elements from a plurality of coil elements for capturing a magnetic resonance tomography recording, FIG. 4 shows a method for providing a trained function for determining an optimized subset of coil elements, FIG. 5 shows a determining system, FIG. 6 shows a training system, FIG. 7 shows a magnetic resonance tomography system.

DETAILED DESCRIPTION

FIG. 1 shows a first exemplary embodiment of a method for determining an optimized subset of coil elements from a plurality of coil elements for capturing a magnetic resonance tomography recording.

The magnetic resonance tomography (MRT) recording is therein captured, for example, with an MRT system 10 according to FIG. 7.

The plurality of coil elements are configured to capture the MRT recording. In particular, the plurality of coil elements are configured to capture a signal from which the MRT recording can be reconstructed. The captured signal is also designated "raw data" below. The MRT recording is also designated medical image data below. The plurality of coil elements can therein be included by one or more local coils 38.

Creation of the signal and the capture of the signal are set out in the description relating to FIG. 7.

The MRT recording is a three-dimensional representation and/or mapping of an examination object 13 and/or a portion of the examination object 13. The examination object 13 is therein, in particular, a human and/or a patient or an animal.

In a method step of a providing PROV-1 of a target volume, the target volume is provided in a scout view.

The scout view is therein an MRT recording, in particular a rapid MRT recording of the examination object 13, in particular a patient. In the scout view, at least one region of the examination object 13 to be investigated is mapped. The scout view can be captured, in particular, with a system coil 20. The scout view can map, in particular, a three-dimensional representation of the region of the examination object 13 to be investigated. The target volume therein defines a region and/or a subregion in the scout view. The target volume can be, in particular, a three-dimensional region in the scout view.

In some embodiments, the target volume can comprise the whole of the region that is mapped in the scout view. In other words, the target volume can comprise a field of view of the scout view.

Alternatively, in some embodiments of the present invention, the target volume can comprise a segmented organ in the scout view. In other words, at least one organ of the examination object 13 represented in the scout view can be segmented manually or automatically. The segmented region of the scout view which maps the at least one organ can correspond to the target volume. The organ can therein be, for example, a liver or a lung or a heart, etc. Alternatively, the organ can also comprise a portion of a skeleton of the examination object 13, for example, one or more vertebrae.

Alternatively, the target volume can comprise a cuboid about a segmented organ mapped in the scout view. In particular, for this purpose, the organ can be configured as described above. The cuboid can therein form a box which, as a maximum, is formed large enough so that it encloses the organ completely. The cuboid can also be designated an organ box.

Alternatively, the target volume can comprise a region in the scout view that is relevant for a diagnostic process. For example, for a diagnosis of a disk prolapse, only the region in which the spinal column and/or a portion of the spinal column is mapped in the scout view may be relevant. An abdominal cavity of the examination object 13 also mapped in the scout view may not be included by the target volume in the example.

In some embodiments of the present invention, the target volume can be determined with a trained function. The trained function can be configured as described above, in general. In particular, the trained function can comprise a neural network. The trained function can therein be configured to determine the target volume dependent upon the scout view and a target of an examination and/or a diagnostic process. For example, the trained function can determine a heart as the target volume if, as input data for the trained function, the scout view of a thorax and the key expression "cardio" are provided. In particular, the trained function can be configured to segment an organ in the scout view that is dependent upon the examination or diagnostic process.

In the method step of providing PROV-1 the target volume, the target volume can be provided by a database via an interface SYS.INF. For example, the target volume can be selected manually by a user, for example, an MTRA or a medical practitioner, in particular, a medical operating personnel member, and provided via a user interface. The user interface can be, for example, a touch-sensitive screen (touchscreen) on which the user can draw in the target volume in the scout view. Alternatively, in the method step of providing PROV-1 the target volume, the target volume can be determined with a computing unit SYS-CU. For example, the target volume can be segmented in an automated manner. In particular, the target volume can be segmented dependent upon an examination and/or a diagnostic process for which the MRT recording is to be created. In particular, the target volume can be segmented via a threshold value segmentation and/or via an application of a trained function.

In a method step of determining DET-1 a plurality of subsets of coil elements, on the basis of the plurality of coil elements, a plurality of subsets of coil elements are determined. Therein, the individual subsets are configured distinct and/or different from one another. In other words, each selection and/or combination of coil elements is unique within a subset in the plurality of subsets. A subset comprises at least one coil element. In particular, a subset can comprise at least two coil elements. In particular, the subset of coil elements then comprises at least two coil elements if the MRT recording is captured via parallel MRT imaging. The method step of determining DET-1 the plurality of subsets can be carried out, in particular, with a computing unit SYS.CU.

In a method step of determining DET-2 at least one quality criterion, for each subset of coil elements, at least one quality criterion is determined. In particular, the quality criterion can be determined with the computing unit SYS.CU. The quality criterion therein relates to an image quality of the MRT recording in the target volume dependent upon the coil elements in the subset. In particular, the quality criterion relates to an expected image quality in the target volume. In other words, the quality criterion of a subset comprises a parameter which defines an image quality which is expected in the target volume in an MRT recording that is captured with the coil elements of the subset.

In some embodiments of the present invention, the quality criterion can relate to an (expected) noise in an MRT recording of this type. In particular, the quality criterion can comprise an (expected) noise level and/or noise quantity in the target volume of such an MRT recording. The noise can comprise, in particular, a spatially resolved noise within the target volume. Alternatively or additionally, the noise can comprise a mean noise and/or a variance of the noise in the target volume.

In particular, the noise can define a system noise and/or a background noise. In other words, the noise can define a noise on the signal captured with the coil elements only with a main magnet field applied and/or without irradiation of an excitation pulse. Alternatively, the noise can comprise and/or define a sensitivity of the coil elements and/or the combination of the coil elements in a corresponding subset. Alternatively or additionally, noise can define a reconstructability of the MRT recording from the captured signal and/or the raw data. In other words, the noise can define an (expected) noise in the reconstructed MRT recording.

In some embodiments of the present invention, the at least one quality criterion of each subset can comprise a g-factor map. The g-factor map defines a reconstructability of an MRT recording from the signal and/or raw data captured with the coil elements of the subset. The g-factor map is, in particular, dependent upon the sensitivities of the individual coil elements of the subset. The g-factor map is, in particular, dependent upon the spatially distributed sensitivities and/or the spatially resolved sensitivities of the coil elements in the subset. The spatially resolved sensitivity of a coil element can be defined via a sensitivity map.

In order to determine the sensitivity map of a coil element, a further scout view can be created. In this scout view, the signal can only be read out and/or captured with the coil element, for which the sensitivity map is to be determined, read out and/or captured. The scout view is, in particular, spatially only slightly resolved. This scout view can be divided by the scout view that was captured with the system coil 20. The quotient then defines the sensitivity map.

In order to determine the g-factor map from more than one coil element, the sensitivity maps of the individual coil elements can be combined with and/or offset against one another. This can take place directly or via reconstruction coefficients of the parallel MRT imaging. In particular, an acceleration factor can be taken into account which specifies a degree of parallelization in the parallel MRT imaging. For an acceleration factor equal to 1, the MRT imaging is not parallelized. The sensitivity maps are offset against one another with regard to their spatial position. Breuer et al. describe in "General Formulation for Quantitative G-Factor Calculation in GRAPPA Reconstructions", Magnetic Resonance in Medicine 62: 739-746 (2009) and Pruessmann et al. describe in "SENSE: Sensitivity Encoding for FAST MRT", Magnetic Resonance in Medicine 42: 952-962 (1999) a significance and/or interpretation of the g-factor maps and how they can be determined.

Alternatively or additionally, the at least one quality criterion for each subset relates to a combined sensitivity map for the coil elements of the subset. The combined sensitivity map of a subset therein defines a spatial distribution of the sensitivity, which is achieved with the combination of the coil elements of the subset.

In order to determine the combined sensitivity map of a subset, in a method step, as described above, a scout view is captured with the system coil. Furthermore, a further scout view is captured with the combination of coil elements of the subset. In order to determine the combined sensitivity map, the scout view of the subset is divided by the scout view of the system coil. In order to capture the scout view of the subset, the captured signal of each coil element can be read out individually. Before the reconstruction of the scout view, the read out signals of the coil elements which are included by the subset are combined with and/or offset against one another according to a known mathematical concept and the combined signal is reconstructed.

In particular, the combined sensitivity map can be determined for all the subsets in parallel. Therein, for each subset, a combined sensitivity map is determined. During parallel determination, the signals of all the coil elements are read out and/or captured. For capturing and/or determining a scout view of a single subset, the read-out signals of the corresponding coil element of the subset are then combined and reconstructed.

In some embodiments of the present invention, the combined sensitivity map of a subset can be put into relation with a noise quantity and/or noise level. The noise level defines a background noise by way of the examination object 13 and/or the surroundings and/or a system noise. In order to determine the noise level of a subset, the examination object 13 is positioned in the MRT system 10. Therein, no excitation pulse is emitted and only the main magnet field acts upon the examination object 13. For each coil element of the subset, a noise signal is read out and/or captured. The noise signals of the coil elements of the subset are combined, as described above in respect of the read-out signals, on capturing the scout view. From this combined noise signal, the noise level is determined. Therein, the noise level relates to a variance or a mean value of the noise level.

In particular, the noise level of the different subsets can be captured and/or determined in parallel. In particular, for this purpose, the noise signals of all the coil elements that are included by at least one subset are read out. When the noise signals are combined, the noise signals of the coil elements which are included by a subset are combined.

In some embodiments of the present invention, the at least one quality criterion of each subset can relate to or comprise a signal-to-noise ratio. For this purpose, for each subset in the corresponding sensitivity map within the target volume, a mean signal and/or a mean signal value can be determined. The mean signal can be determined for the entire target volume or for a portion of the target volume. The signal-to-noise ratio of a subset defines the quotient of the mean signal and the noise level of the subset.

In some embodiments, with the quality criterion of a subset, a duration and/or a recording duration for capturing the MRT recording with the subset of coil elements can also be taken into account. If the recording duration of the MRT recording with a subset of coil elements exceeds a threshold value, it can lead to a worsening of the quality criterion of the subset.

In a method step of determining DET-3 the optimized subset, the subset optimized for capturing the MRT recording is determined dependent upon the corresponding quality criteria. In particular, for determining the optimized subset, an optimized subset quality criterion can be determined. The optimized subset is then the subset to which the corresponding optimized quality criterion is assigned and/or for which the corresponding optimized quality criterion has been determined.

The optimized quality criterion can, in particular, be determined by comparing the quality criteria of all subsets.

In some embodiments, the optimized quality criterion can be the quality criterion of the quality criteria of all the subsets, according to which the noise is at a minimum. In other words, an expected image quality of the MRT recording captured with the corresponding optimized subset of coil elements is the best by comparison.

In some embodiments of the present invention, the image quality can be optimized taking account of the recording duration with the optimized subset.

In a method step of providing an information item as to which of the plurality of coil elements is and/or are included by the optimized subset, the information item is provided to the user and/or the MRT system 10. In particular, the information item thus states which coil elements of the plurality of coil elements should advantageously be read out in order to capture the MRT recording with the best possible image quality.

FIG. 2 shows a second exemplary embodiment of a method for determining an optimized subset of coil elements from a plurality of coil elements for capturing a magnetic resonance tomography recording.

The second exemplary embodiment comprises, in addition to the method steps set out in the description of FIG. 1, a method step of capturing REC the MRT recording with the optimized subset of coil elements. In particular, during capturing REC of the MRT recording, the coil elements and/or the at least one included coil element that are included by the optimized subset are read out. In other words, the capturing REC of the MRT recording comprises a method step of reading out the optimized subset of coil elements.

The capture REC of the MRT recording also comprises a method step of reconstructing the MRT recording from the signal captured with the optimized subset and/or from the raw data. In particular, the reconstruction can be based upon a filtered back projection.

FIG. 3 shows a third exemplary embodiment of a method for determining an optimized subset of coil elements from a plurality of coil elements for capturing a magnetic resonance tomography recording.

The third exemplary embodiment comprises, in addition to the method steps set out in the description relating to FIGS. 1 and 2, a method step of applying APP a trained function. The method step of applying APP the trained function is therein included by the method step of determining DET-3 the optimized subset. Therein, the optimized quality criterion is determined. The optimized subset is then the subset of the plurality of subsets corresponding to or assigned to the optimized quality criterion. In other words by way of applying APP the trained function to the quality criteria, the optimized subset is determined indirectly.

The quality criteria of the plurality of subsets are therefore input data of the trained function. Output data of the trained function comprises the optimized quality criterion.

FIG. 4 shows a method for providing a trained function for determining an optimized subset of coil elements.

In particular, the trained function is designed to determine the optimized subset according to the description regarding FIG. 3. In particular, the optimized subset is determined indirectly by applying APP the trained function, at least indirectly. The trained function determines the optimized quality criterion which is assigned to the optimized subset.

The method comprises a method step of providing TPROV-1 a plurality of training quality criteria. In particular, the providing of the plurality of training quality criteria comprises a receiving or an accessing. Each training quality criterion is therein assigned to a planned MRT recording from a plurality of planned MRT recordings. In particular, an MRT recording can be assigned to more than one training quality criterion. The different MRT recordings can relate, for example, to different regions or portions of the examination object 13 or different recording protocols or different examination objects 13 or different examination goals and/or purposes. In particular, the plurality of planned MRT recordings can comprise fewer planned MRT recordings than the plurality of training quality criteria. The training quality criteria are therein configured similarly to the quality criteria described in relation to FIG. 1. A training subset of coil elements can therein be assigned to each training quality criterion. The different training quality criteria of a planned MRT recording describe an expected image quality of the planned MRT recording if the planned MRT recording is captured with the assigned training subset of coil elements.

The method further comprises a method step of providing TPROV-2 a plurality of optimized training quality criteria. In particular, the providing of the plurality of optimized training quality criteria can comprise a receiving or an accessing. Therein, for each planned MRT recording of the plurality of planned MRT recordings, exactly one optimized training quality criterion is provided. The optimized training quality criteria are therein included by the plurality of training quality criteria. An optimized training quality criterion is an optimized quality criterion configured as in relation to FIG. 1. In particular, the optimized training quality criterion of a planned MRT recording corresponds to the training quality criterion, which defines the comparatively best expected image quality for the planned MRT recording. The optimized training quality criteria can have been selected, in particular, by an experienced user from the plurality of training quality criteria.

In a method step of training TRAIN a function, the function is trained dependent upon the plurality of training quality criteria and the plurality of optimized training quality criteria. In particular, the function for training APP is applied to the plurality of training quality criteria. Therein, for each planned MRT recording of the associated training quality criteria, a preliminary optimized training quality criterion is selected and/or determined. This preliminary optimized training quality criterion is aligned with the optimized training quality criterion of the corresponding planned MRT recording that is provided. If the comparison produces a negative result, if therefore the two optimized quality criteria do not match, the function is modified and/or adjusted. This modification defines the training of the function. The function is modified until the preliminary optimized training quality criteria, which are determined by way of the application of the function, correspond to the optimized training quality criteria provided or until at least one particular proportion thereof match one another.

In a method step of providing TPROV-3 the trained function, the function trained in this way is provided.

FIG. 5 shows a determining system SYS for determining an optimized subset of coil elements from a plurality of coil elements for capturing a magnetic resonance tomography recording and FIG. 6 shows a training system TSYS for provision of a trained function.

The determining system SYS shown for determining an optimized subset of coil elements from a plurality of coil elements for capturing a magnetic resonance tomography recording is designed to carry out a method, according to one or more example embodiments of the present invention, for determining an optimized subset of coil elements from a plurality of coil elements for capturing a magnetic resonance tomography recording. The training system TSYS shown is configured to carry out a method, according to one or more example embodiments of the present invention, for providing the trained function. The determining system SYS comprises an interface SYS.IF, a computing unit SYS.CU and a memory unit SYS.MU. The training system TSYS comprises a training interface TSYS.IF, a training computing unit TSYS.CU and a training memory unit TSYS.MU.

The determining system SYS and/or the training system TSYS can be, in particular, a computer, a microcontroller or an integrated circuit (IC). Alternatively, the determining system SYS and/or the training system TSYS can be a real or virtual computer network (a technical term for a real computer network is a "cluster" and a technical term for a virtual computer network is a "cloud"). The determining system SYS and/or the training system TSYS can be configured as a virtual system which is executed on a computer or a real computer network or a virtual computer network (a technical term for this is "virtualization").

The interface SYS.IF and/or the training interface TSYS.IF can be a hardware or software interface (for example, a PCI bus, a USB or a Firewire). The computing unit SYS.CU and/or the training computing unit TSYS.CU can comprise hardware and/or software constituents, for example, a microprocessor or a so-called field-programmable gate array (FPGA). The memory unit SYS.MU and/or the training memory unit TSYS.MU can be realized as a non-permanent working memory (Random Access Memory, (RAM)) or as a permanent mass storage unit (hard disk, USB stick, SD card, solid state disk (SSD)).

The interface SYS.IF and/or the training interface TSYS.IF can, in particular, comprise a plurality of subinterfaces which carry out different method steps of the respective method according to one or more example embodiments of the present invention. In other words, the interface SYS.IF and/or the training interface TSYS.IF can be designed as a plurality of interfaces SYS.IF and/or training interfaces TSYS.IF. The computing unit SYS.CU and/or the training computing unit TSYS.CU can comprise, in particular, a plurality of computing sub-units which carry out different method steps of the respective method according to one or more example embodiments of the present invention. In other words, the computing unit SYS.CU and/or the training computing unit TSYS.CU can be configured as a plurality of computing units SYS.CU and/or training computing units TSYS.CU.

FIG. 7 shows a magnetic resonance tomography system 10. The MRT system 10 is shown schematically. The MRT system 10 comprises a scanner unit 11 formed by a magnet unit. In addition, the MRT system 10 has a receiving region 12 for receiving an examination object 13, in particular a patient. The receiving region 12 in the present exemplary embodiment is configured as cylindrical and is surrounded cylindrically in a circumferential direction by the scanner unit 11, in particular the magnet unit. In principle, however, an embodiment of the receiving region 12 deviating therefrom is readily conceivable. The examination object 13 can be pushed and/or moved via a positioning apparatus 14 of the MRT system 10 into the receiving region 12. For this purpose, the positioning apparatus 14 has a support 15 which is configured able to be moved within the receiving region 12. In particular, the support 15 is mounted to be movable in the direction of a longitudinal extent of the receiving region 12 and/or in the z-direction.

The scanner unit 11, in particular, the magnet unit comprises a superconducting main magnet 16 for generating a strong and, in particular, constant main magnet field 17. Furthermore, the scanner unit 11, in particular the magnet unit, has a gradient coil unit 18 for generating magnetic field gradients that are used for position encoding during an imaging process. The gradient coil unit 18 is actuated via a gradient control unit 19 of the MRT system 10. The scanner unit 11, in particular, the magnet unit further comprises a high frequency antenna unit and/or a system coil 20 for exciting a polarization which forms in the main magnet field 17 generated by the main magnet 16. The system coil 20 is therein firmly arranged within the scanner unit 11, in particular the magnet unit. The system coil 20 is controlled by a system coil control unit 21 of the MRT system 10 and radiates high frequency magnetic resonance sequences into the receiving region 12 of the magnetic resonance apparatus 10.

For capturing magnetic resonance signals, the MRT system 10 has at least one local high frequency coil and/or local coil 38 which can be positioned about a region to be investigated of the examination object 13. A selection of a local coil 38 for the current magnetic resonance examination takes place dependent upon the region to be investigated of the examination object 13. For example, a local head high frequency coil for a head examination or a local knee high frequency coil for a knee examination, etc. The local coil 38 therein comprises at least one coil element as described above. In particular, if the local coil 38 comprises more than one coil element, the coil elements of the local coil 38 can be read out and/or controlled individually.

For controlling the main magnet 16, the gradient control unit 19 and, for controlling the system coil control unit 21, the MRT system 10 has a system control unit 22. The system control unit 22 centrally controls the MRT system 10, for example, the execution of a pre-determined imaging gradient echo sequence. In addition, the system control unit 22 comprises an evaluation unit (not shown in detail) for evaluating MRT recordings and/or medical image data which is captured during the magnetic resonance examination.

Furthermore, the MRT system 10 comprises a user interface 23 which is connected to the system control unit 22. Control information such as, for example, imaging parameters and reconstructed MRT recordings can be displayed on a display unit 24, for example, on at least one monitor, of the user interface 23 for a user and/or a medical operating personnel member. In addition, the user interface 23 has an input unit 25 via which the information and/or parameters can be input by the user during a measurement procedure.

The scanner unit 11 of the MRT system 10 is arranged together with the positioning device 14 within an examination room 26. By contrast, the system control unit 22 is arranged together with the user interface 23 within a control room 27. The control room 27 is provided separately from the examination room 26. In particular, the examination room 26 is screened from the control room 27 in respect of high frequency radiation. During a magnetic resonance examination and/or a capture of an MRT recording, the examination object 13 is situated within the examination room 26, whereas the user is within the control room 27.

The MRT system 10 shown can naturally comprise further components that MRT systems 10 typically have. A general functional principle of the MRT system 10 is also known to a person skilled in the art, so that a detailed description of the further components is dispensed with.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where it has not yet explicitly been set out, although useful and in the spirit of the present invention, individual exemplary embodiments, individual sub-aspects or features thereof can be combined and/or exchanged with one another without departing from the scope of the present invention. Advantages of the present invention described in relation to an exemplary embodiment also apply, where transferrable, to other exemplary embodiments without this being explicitly stated.

What is claimed is:

1. A non-transitory computer-readable storage medium storing program portions that, when executed by a determining system, cause the determining system to perform a method for determining a subset of coil elements, from among a plurality of coil elements, for capturing a magnetic resonance tomography recording, the method comprising:
- providing a target volume in a scout view;
- determining a plurality of subsets of coil elements from among the plurality of coil elements, wherein individual subsets, from among the plurality of subsets, are configured different from one another;
- determining at least one quality criterion for each of the plurality of subsets of coil elements, wherein the at least one quality criterion of a corresponding subset of coil elements relates to an image quality in the target volume, dependent upon the corresponding subset of coil elements;
- determining the subset of coil elements, from among the plurality of subsets of coil elements, by applying a trained function to the at least one quality criterion for each of the plurality of subsets of coil elements, to determine an optimized quality criterion, wherein the subset of coil elements is a subset of coil elements corresponding to the optimized quality criterion; and
- providing an information item regarding which of the plurality of coil elements are included in the subset of coil elements.

2. The non-transitory computer-readable storage medium of claim 1, wherein the method further comprises:
- capturing the magnetic resonance tomography recording with the subset of coil elements.

3. The non-transitory computer-readable storage medium of claim 2, wherein the at least one quality criterion of the corresponding subset of coil elements relates to noise in a magnetic resonance tomography recording captured with the corresponding subset of coil elements.

4. The non-transitory computer-readable storage medium of claim 1, wherein the target volume comprises:
- a field of view of the scout view;
- a segmented organ mapped in the scout view;
- a cuboid round the segmented organ mapped in the scout view; or
- a region in the scout view that is relevant for a diagnostic process.

5. The non-transitory computer-readable storage medium of claim 1, wherein the at least one quality criterion of the corresponding subset of coil elements relates to noise in a magnetic resonance tomography recording captured with the corresponding subset of coil elements.

6. The non-transitory computer-readable storage medium of claim 5, wherein the subset of coil elements comprises
- a subset of coil elements for which the noise is at a minimum compared with quality criteria of others of the plurality of subsets of coil elements.

7. The non-transitory computer-readable storage medium of claim 5, wherein the at least one quality criterion for each subset of coil elements includes a g-factor map.

8. The non-transitory computer-readable storage medium of claim 5, wherein the at least one quality criterion for each subset of coil elements relates to a combined sensitivity map for coil elements in the subset of coil elements.

9. The non-transitory computer-readable storage medium of claim 1, wherein the at least one quality criterion for each subset of coil elements includes a g-factor map.

10. The non-transitory computer-readable storage medium of claim 1, wherein the at least one quality criterion for each subset of coil elements relates to a combined sensitivity map for coil elements in the subset of coil elements.

11. A non-transitory computer-readable storage medium storing program portions that, when executed by a determining system, cause the determining system to perform a method for providing a trained function for determining a subset of coil elements, the method comprising:
- providing a plurality of training quality criteria, wherein each training quality criterion of a planned magnetic resonance tomography recording is assigned from a plurality of planned magnetic resonance tomography recordings;
- providing a plurality of optimized training quality criteria, wherein, for each of the plurality of planned magnetic resonance tomography recordings, an optimized training quality criterion is provided, and wherein the plurality of optimized training quality criteria are included by the plurality of training quality criteria;
- training a function based on the plurality of training quality criteria and the plurality of optimized training quality criteria; and
- providing the trained function.

12. A determining system to determine a subset of coil elements, from among a plurality of coil elements, for capturing a magnetic resonance tomography recording, the determining system comprising:
- an interface configured to provide a target volume in a scout view, and to provide an information item regarding which of the plurality of coil elements are included in the subset of coil elements; and
- at least one processor configured to execute computer-executable instructions to
  - determine a plurality of subsets of coil elements from among the plurality of coil elements, wherein individual subsets of coil elements, from among the plurality of subsets of coil elements, are configured different from one another,
  - determine at least one quality criterion for each of the plurality of subsets of coil elements, wherein the at least one quality criterion for a corresponding subset of coil elements relates to an image quality in the target volume, dependent upon the corresponding subset of coil elements, and
  - determine the subset of coil elements, from among the plurality of subsets of coil elements, by applying a trained function to the at least one quality criterion for each of the plurality of subsets of coil elements, to determine an optimized quality criterion, wherein the subset of coil elements is a subset of coil elements corresponding to the optimized quality criterion.

13. A magnetic resonance tomography system comprising:
- the determining system as claimed in claim 12, wherein the magnetic resonance tomography system is configured to capture the magnetic resonance tomography recording with the subset of coil elements.

* * * * *